(12) United States Patent
Austin

(10) Patent No.: US 8,522,366 B2
(45) Date of Patent: Sep. 3, 2013

(54) SOCK STRUCTURE AND METHOD OF USE

(76) Inventor: Lenora Austin, Tucson, AZ (US)

( * ) Notice: Subject to any disclaimer, the term of this patent is extended or adjusted under 35 U.S.C. 154(b) by 147 days.

(21) Appl. No.: 12/954,313

(22) Filed: Nov. 24, 2010

(65) Prior Publication Data

US 2012/0124717 A1    May 24, 2012

(51) Int. Cl.
*A43B 17/00*    (2006.01)
(52) U.S. Cl.
USPC ............................................................ 2/239
(58) Field of Classification Search
USPC ............... 2/239, 240, 241; 602/14, 48, 7, 602/66; 607/108, 112, 114; 604/291
See application file for complete search history.

(56) References Cited

U.S. PATENT DOCUMENTS

| | | | | |
|---|---|---|---|---|
| 2,949,914 A * | 8/1960 | Waldrum | ........................ | 607/111 |
| 3,266,058 A * | 8/1966 | Guttman | ........................... | 2/239 |
| 3,628,537 A * | 12/1971 | Berndt et al. | ................. | 607/112 |
| 3,648,291 A * | 3/1972 | Pankers | ............................... | 2/16 |
| 3,900,035 A * | 8/1975 | Welch et al. | .................... | 607/108 |
| 3,990,440 A * | 11/1976 | Gaylord, Jr. | .................... | 128/892 |
| 4,055,188 A * | 10/1977 | Pelton | ............................ | 607/112 |
| 4,150,442 A * | 4/1979 | Boone | .............................. | 602/63 |
| 4,190,054 A * | 2/1980 | Brennan | ........................ | 607/112 |
| 4,671,267 A * | 6/1987 | Stout | ................................ | 602/2 |
| 4,922,929 A * | 5/1990 | DeJournett | .................... | 128/892 |
| 4,938,222 A * | 7/1990 | Bier, Jr. | .......................... | 607/111 |
| 4,976,262 A * | 12/1990 | Palmacci | ....................... | 607/108 |
| 5,170,783 A * | 12/1992 | Smith | ........................... | 607/104 |
| 5,187,814 A | 2/1993 | Gold | | |
| 5,456,704 A * | 10/1995 | Kilcullen | ....................... | 607/111 |
| 5,591,221 A * | 1/1997 | Owens | ........................... | 607/111 |
| 5,873,903 A | 2/1999 | Garcia | | |
| 5,921,243 A * | 7/1999 | Shakoor | ......................... | 128/882 |
| 6,001,122 A * | 12/1999 | Lyles | .............................. | 607/111 |
| 6,230,501 B1 * | 5/2001 | Bailey et al. | ................... | 62/51.1 |
| 6,598,235 B2 | 7/2003 | Bulla | | |
| 6,865,825 B2 * | 3/2005 | Bailey et al. | ....................... | 36/88 |
| 7,056,299 B2 * | 6/2006 | Brown et al. | ................... | 602/61 |
| 7,060,086 B2 | 6/2006 | Wilson et al. | | |
| 7,107,706 B1 * | 9/2006 | Bailey et al. | ....................... | 36/88 |
| 7,204,041 B1 * | 4/2007 | Bailey et al. | ....................... | 36/29 |
| 7,481,786 B2 * | 1/2009 | Flick et al. | ..................... | 602/65 |
| 7,621,944 B2 | 11/2009 | Wilson et al. | | |

(Continued)

FOREIGN PATENT DOCUMENTS

GB    2407961 A    5/2005

OTHER PUBLICATIONS http://www.heatpacksuk.co.uk/heated-thermal-socks.php.
http://www.tmlabs.co.uk/heated-thermal-socks.html.

*Primary Examiner* — Alissa L Hoey

(57) ABSTRACT

A method of applying a cold pack to a wearer undergoing chemotherapy treatment using a sock structure. The sock structure comprises a sock body that includes a foot portion configured to covering the wearer's foot, a leg portion covering a portion of the wearer's ankle and leg, and a turned heel that provides an angular junction between the foot and leg portions. The sock structure comprises a pocket integral with the sock body and located along the bottom of the foot portion and the turned heel. The pocket is configured for receiving the cold pack and supporting the cold pack along the bottom of the foot portion and the turned heel, with the cold pack in heat transmitting relation with the sole and heel of a human foot located in the sock body.

3 Claims, 2 Drawing Sheets

(56) References Cited

U.S. PATENT DOCUMENTS

| | | | |
|---|---|---|---|
| 7,704,273 B1* | 4/2010 | Morris et al. | 607/111 |
| 7,806,841 B2* | 10/2010 | Caselnova | 602/2 |
| 8,205,271 B2* | 6/2012 | Canci | 2/239 |
| 2002/0019657 A1* | 2/2002 | Elkins | 607/111 |
| 2003/0163182 A1* | 8/2003 | Hickey | 607/108 |
| 2003/0195439 A1* | 10/2003 | Caselnova | 601/15 |
| 2004/0039432 A1* | 2/2004 | Warriner | 607/108 |
| 2004/0049253 A1* | 3/2004 | Bryant | 607/108 |
| 2004/0073281 A1* | 4/2004 | Caselnova | 607/111 |
| 2004/0158283 A1 | 8/2004 | Shook et al. | |
| 2005/0101828 A1 | 5/2005 | Butler et al. | |
| 2005/0177215 A1* | 8/2005 | Rosenberg | 607/111 |
| 2006/0218692 A1 | 10/2006 | Lamarque | |
| 2006/0253962 A1* | 11/2006 | Hua | 2/239 |
| 2007/0135777 A1 | 6/2007 | Greene et al. | |
| 2008/0040831 A1* | 2/2008 | Nilforushan et al. | 2/69 |
| 2008/0077213 A1* | 3/2008 | Vickroy | 607/108 |
| 2008/0125842 A1 | 5/2008 | Petitt | |
| 2008/0183118 A1 | 7/2008 | Weinberg et al. | |
| 2009/0120126 A1* | 5/2009 | Mew | 62/530 |
| 2009/0125086 A1* | 5/2009 | Juta et al. | 607/108 |
| 2009/0137938 A1 | 5/2009 | Parivash | |
| 2009/0292343 A1 | 11/2009 | Sternlight | |
| 2010/0050322 A1* | 3/2010 | Zagula | 2/239 |
| 2011/0061148 A1* | 3/2011 | Egozi | 2/239 |
| 2012/0010550 A1* | 1/2012 | Weinberg et al. | 602/63 |

\* cited by examiner

SOCK STRUCTURE AND METHOD OF USE

INTRODUCTION AND SUMMARY OF THE PRESENT INVENTION

The present invention relates to a new and useful sock structure, that is especially useful in applying a cold pack to a cancer patient undergoing chemotherapy treatment, and to a method of applying a cold pack to a wearer (e.g. a cancer patient undergoing chemotherapy treatment), using the sock structure.

The present invention was designed primarily to help chemotherapy patients handle the side effect of a condition known as "hand-foot syndrome". Hand foot syndrome is a condition that results in sensitivity in a patient's feet, and other appendages, from leakage of chemotherapy agent during treatment (also referred to as "infusion"). By applying a cold pack to each of the patient's feet during the chemotherapy infusion, the effects of the hand-foot syndrome are greatly reduced because the walls of the capillaries are condensed from the cold, and thereby reduces the prospects of leakage of chemotherapy agent. The present invention has been designed to make it more comfortable for patients to wear a cold pack on their feet for an extended periods of time, and to otherwise provide as much comfort as possible for the patient. For example, rather than having to place their feet on the cold pack on a footrest, the sock structure and method of the present invention allows the patient to place the cold pack on the feet, in a way that allows greater mobility for the patient (e.g. it allows the patient to cross legs while maintaining cold on feet, during the chemotherapy treatment).

More specifically, The present invention provides a new and useful sock structure, which is especially useful in applying a cold pack to a cancer patient undergoing chemotherapy treatment, and to a method of applying a cold pack to a wearer (e.g. a cancer patient undergoing chemotherapy treatment), using the sock structure. The sock structure comprises a sock body that includes (i) a foot portion configured to cover substantially all of the wearer's foot, (ii) a leg portion configured to cover a portion of the wearer's ankle and leg, and (iii) a turned heel that provides an angular (turned) junction between the foot and leg portions. Moreover, the sock structure comprises a pocket integral with the sock body and located along predetermined portions of the bottom of the foot portion and the turned heel. The pocket is connected with the sock body in a manner that provides heat transmitting relationship between the pocket and the sole and heel of a human foot and heel located in the sock body, and the pocket is configured for receiving a cold pack and supporting the cold pack along the bottom of the foot portion and a predetermined portion of the turned heel, with the cold pack in heat transmitting relation with the sole and heel of a human foot located in the sock body. The leg portion of the sock body has an opening through which a human foot and heel can be inserted into the sock body with the heel of the foot located in the turned heel of the sock body, and the pocket has at least one separate opening for receipt of a cold pack with at least a portion of the cold pack located adjacent to the sole of the foot and a predetermined portion of the heel of the human foot.

Preferably, each of the sock body and pocket are formed of fabric material. Moreover, the pocket is formed by a segment of material that is secured to the bottom of the foot portion and turned heel and combines with the bottom of the foot portion and turned heel to form the pocket, as well as a pair of openings that enable convenient access for insertion of a cold pack into the pocket.

The sock structure is particularly effective in providing cold pack therapy to a patient undergoing chemotherapy treatment. Preferably, the sock structure is applied to the patient (by the patient inserting his/her foot through the opening in the leg portion, so that the patient's foot is located in the foot portion and the patient's heel is located in the turned heel of the sock body). The cold pack is inserted into the pocket (e.g. through either of the 2 openings in the pocket), either before the chemotherapy agent is administered, or as the chemotherapy agent is being administered, so that the cold pack is located adjacent the patient's sole and heel, either before or as the chemotherapy treatment is started. The cold pack is in heat transmitting relation to the sole and the heel of the cancer patient undergoing chemotherapy treatment, and functions to effectively "apply cold" to the patient's soles and heels, to restrict the patient's capillaries, and thereby reduce risk of leakage of chemotherapy agent from the capillaries during the chemotherapy treatment. The way the cold pack works is to enable heat from the patient's sole and heel to be transferred to the cold pack, which is well known as the way a cold pack functions to cool an object. Thus, a cold pack being in "heat transmitting relationship" with a sole and/or heel of a patient's foot means that the cold pack is located so that heat is effectively and efficiently transferred from the patient's foot to the cold pack, thereby to cool the patient's foot.

These and other features of the present invention will become further apparent from the following detailed description and the accompanying drawings.

DETAILED DESCRIPTION

As described above, the present invention provides a new and useful sock structure and cold pack treatment method, which are particularly useful for a cancer patient undergoing chemotherapy treatment. The principles of the present invention are described herein in connection with a sock structure and cold pack treatment method for a cancer patient undergoing chemotherapy treatment, and from that description the manner in which the principles of the present invention can be used to create and use sock structure for persons with needs comparable to cancer patients undergoing chemotherapy will be apparent to those in the art.

Figure 1:
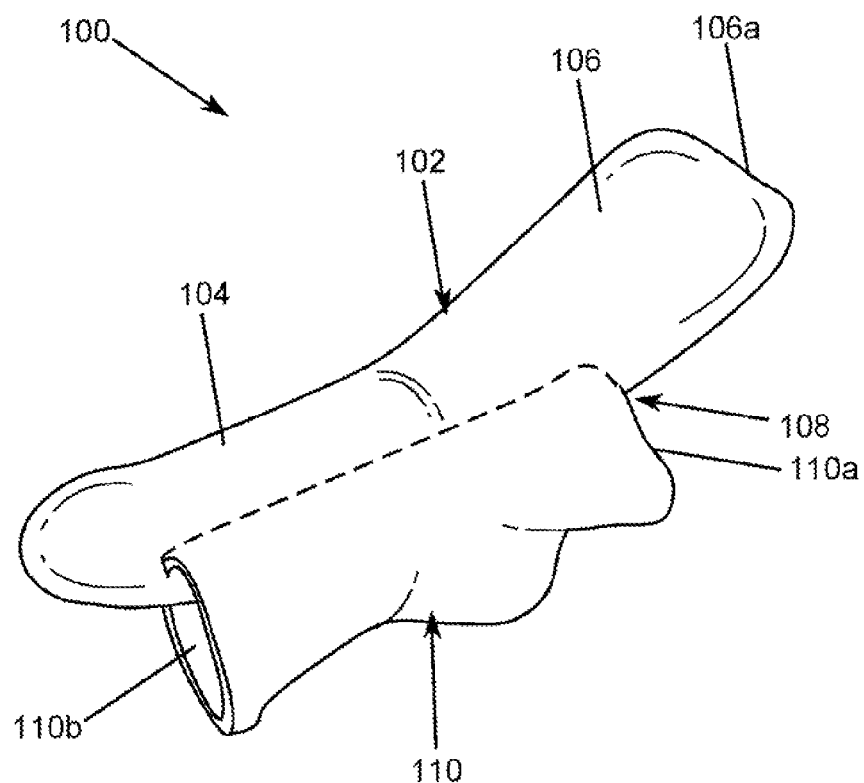
FIG. 1 is an illustration of the sock structure of the present invention, before insertion of a cold pack into the pocket of the sock structure.
Figure 2:
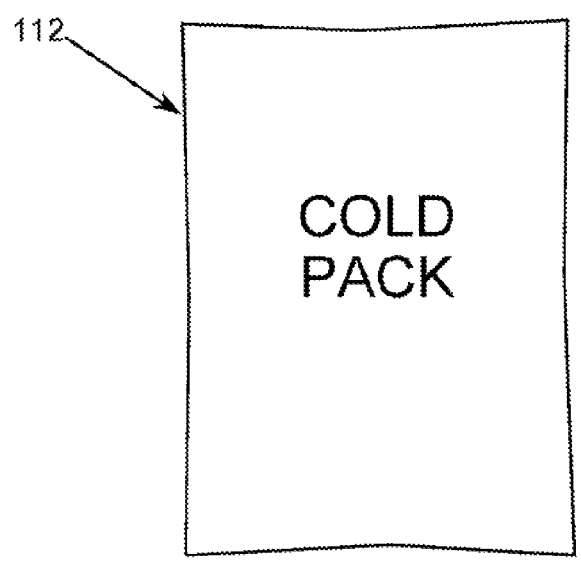
FIG. 2 is an illustration of a typical cold pack that can be used with the sock structure and method according to the principles of the present invention.

FIG. 1 illustrates a sock structure 100, according to the principles of the present invention. The sock structure 100 comprises a sock body 102 that includes a foot portion 104 configured to cover substantially all of the wearer's foot, a leg portion 106 configured to cover a portion of the wearer's ankle and leg, and a turned heel 108 that provides an angular (turned) junction between the foot and leg portions. The sock structure 100 includes a pocket 110 integral with the sock body and located along predetermined portions of the bottom of the foot portion and the turned heel. The pocket 110 is connected with the sock body in a manner that provides heat transmitting relationship between the sole and heel of a human foot and heel located in the sock body and a cold pack located in the pocket, and the pocket is configured for receiving a cold pack 112 (FIG. 2) and supporting the cold pack along the bottom of the foot portion and a predetermined portion of the turned heel, with the cold pack in heat transmitting relation with the sole and heel of a human foot located in the sock body (see FIG. 3).

Figure 3:
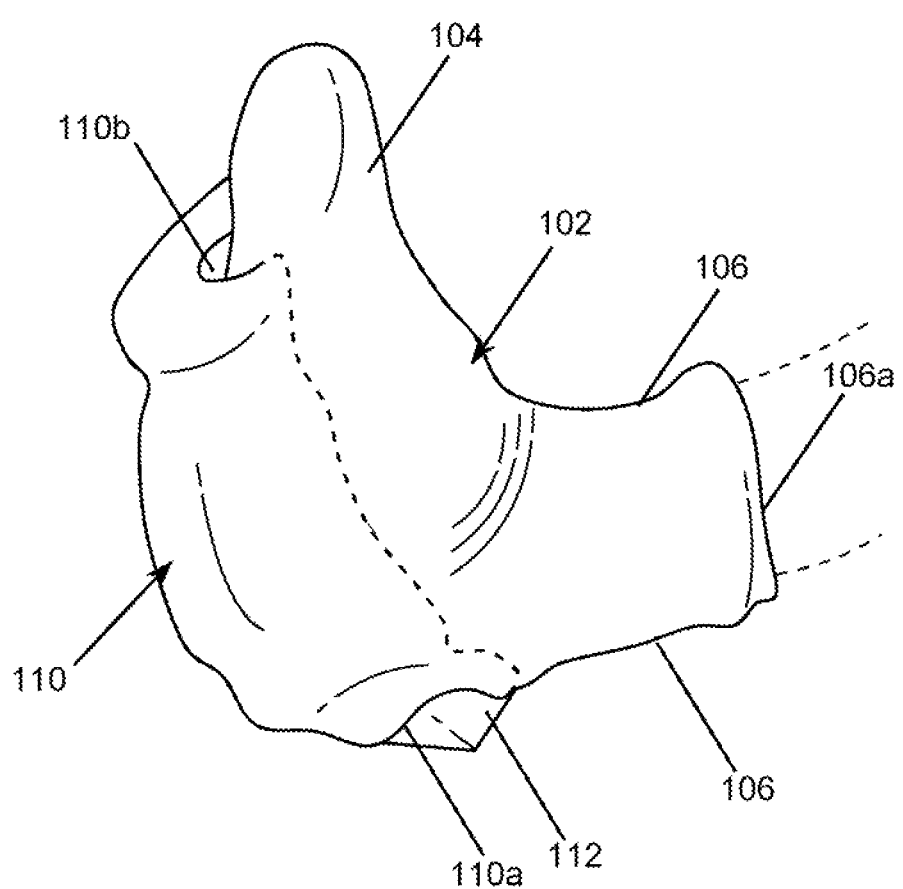
FIG. 3 is an illustration of a patient (e.g. a chemotherapy patient) wearing the socket structure while a cold pack is applied to the patient's sole and heel, according to the principles of the present invention.

The leg portion 106 has an opening 106a through which a human foot and heel can be inserted into the sock body with the heel of the foot located in the turned heel of the sock body, and the pocket 110 a pair of separate openings 110a, 110b, each of which allows insertion of a cold pack into the pocket 110 with at least a portion of the cold pack located adjacent to the sole of a foot and a predetermined portion of the heel of the foot (see FIG. 3). Each of the sock body and pocket are preferably formed of fabric material (e.g. of the type that would typically be used to form a sock). Moreover, the pocket 110 is preferably formed by a segment of material 112 that is secured to the bottom of the foot portion and turned heel of the sock body and combines with the bottom of the foot portion and turned heel to form the pocket and the pair of openings 110a, 110b. The openings 110a, 110b enable the cold pack 112 to be inserted into the pocket from either the opening 110a or the opening 110b.

In using the sock structure with a patient undergoing chemotherapy treatment, the patient would insert his/her foot into the sock body 102, so that the patient's foot is located in the foot portion and the patient's heel is located in the turned heel of the sock body. The cold pack 112 is inserted into the pocket 110, through one of the openings 110a, 110b in the pocket, at a time that is convenient to the chemotherapy, and preferably prior to the chemotherapy treatment. Thus, the patient's foot, with the cold pack therapy in place, would look like that shown in FIG. 3, prior to the administration of the chemotherapy treatment. The cold pack 112 would be in heat transmission relationship with the sole and heel of the patient's foot. The sock structure 100 would remain in place during the chemotherapy treatment (and as long after the treatment as the patient would prefer, or the patient's physician might prescribe).

The present invention is particularly useful to a cancer patient undergoing chemotherapy treatment. The cold pack 112 is in heat transmitting relation to the sole and the heel of a cancer patient undergoing chemotherapy treatment. The cold pack restricts the patient's capillaries, and thereby reduces the likelihood of leakage of chemotherapy agent from the patient's capillaries. Leakage of chemotherapy agent during treatment, can lead to a condition known as hand foot syndrome, where the patient's skin becomes very sensitive, the patient's gripping power is reduced, and the patient's walking power is reduced. Also, the patient's heel can become highly sensitive. Thus, by reducing potential for leakage of chemotherapy agent, the present invention provides a particular benefit to a cancer patient undergoing chemotherapy treatment. In addition, by providing the cold pack 112 in the specially designed sock structure 100, the cancer patient has considerable foot mobility during the chemotherapy treatment (e.g. the patient can cross his/her legs during the treatment).

In the sock structure illustrated and cold pack shown in the figures, the sock body is approx. 13" long, 3½" wide while flat. The pocket is 8" long, 4½" wide. The cold pack is a typical cold pack and in the illustrated example is approximately 5½" by 9". These are example dimensions, which may vary depending on factors such as the foot size of the patient, the size of the cold pack required for the length of time the patient needs the cold pack, etc.

Thus, the foregoing description provides a sock structure and method of applying cold pack therapy to a wearer, that is particularly useful for a cancer patient undergoing chemotherapy treatment, and which would also be particularly useful for treatment of a patient with comparable issues to a patient undergoing chemotherapy treatment. With the foregoing principles in mind, the manner in which a sock structure can be designed and used in the treatment of patients with conditions requiring treatment comparable to chemotherapy will be apparent to those in the art.

The invention claimed is:

1. A method of providing a temperature gradient from a cold pack to a human foot and heel, during treatment of a patient undergoing chemotherapy treatment, comprising:

(a) providing a sock; the sock consisting of a sock body having a leg portion, a foot portion, a turned heel, a toe portion with a closed end and a leg opening; the foot portion having a top surface and a bottom surface, the turned heel having an angular junction between the foot portion and the leg portion, the leg portion extending upwardly from the turned heel portion to the leg opening for insertion of a human foot; and a pocket permanently attached to the bottom surface of the foot portion and to the turned heel portion, the pocket having a first opening and a second opening, the pocket having a length and a width, the length of the pocket extending from the turned heel to the bottom surface of the foot portion adjacent to the toe portion; the first opening located at an end of the length at the turned heel and the second opening located at an opposite end of the length at the bottom surface of the foot portion;

b) providing a cold pack;

(c) inserting a human foot and heel into the sock body; and (d) inserting a cold pack into the pocket, through at least one of the first opening or the second opening during chemotherapy treatment, the cold pack being in heat transmission relationship with a sole and heel of the human foot through the bottom of the foot portion and the turned heel portion of the sock body during the chemotherapy treatment, to relieve the effects of hand-foot syndrome.

2. The method of claim 1, wherein the pocket is formed by a segment of material that is secured to the bottom of the foot portion and turned heel and combines with the bottom of the foot portion and turned heel to form the pocket.

3. The method of claim 2, wherein each of the sock body and pocket are formed of fabric material.

* * * * *